United States Patent [19]

Kawasaki

[11] Patent Number: 5,483,350
[45] Date of Patent: Jan. 9, 1996

[54] OPTICAL SYSTEM FOR INFRARED SPECTROSCOPY HAVING AN ASPHERICAL CONCAVE MIRROR

[75] Inventor: Kazuhiro Kawasaki, c/o JASCO Corporation, 2967-5, Ishikawa-cho, Hachioji-shi, Tokyo 192, Japan

[73] Assignee: Kazuhiro Kawasaki, Kachioji, Japan

[21] Appl. No.: 328,087

[22] Filed: Oct. 24, 1994

[30] Foreign Application Priority Data

Oct. 25, 1993 [JP] Japan ................................ 5-288591

[51] Int. Cl.⁶ ........................ G01N 21/55; G01N 21/01
[52] U.S. Cl. .......................... 356/445; 356/446; 356/244
[58] Field of Search ........................ 356/244, 445–446; 359/850, 853, 856–859, 861

[56] References Cited

U.S. PATENT DOCUMENTS

| | | | |
|---|---|---|---|
| 4,479,058 | 10/1984 | Gast et al. | 356/244 |
| 4,747,684 | 5/1988 | Weiser | 356/446 |
| 5,019,715 | 5/1991 | Sting et al. | 356/445 |
| 5,035,863 | 7/1991 | Finlan et al. | 356/445 |
| 5,064,619 | 11/1991 | Finlan | 356/445 |
| 5,093,580 | 3/1992 | Sting | 356/445 |
| 5,106,196 | 4/1992 | Brierley | 356/445 |
| 5,392,175 | 2/1995 | Reisser | 356/446 |

FOREIGN PATENT DOCUMENTS

| | | | |
|---|---|---|---|
| 0489588 | 6/1992 | European Pat. Off. | 356/445 |
| 57-019647 | 2/1982 | Japan . | |
| 5340870 | 12/1993 | Japan . | |

*Primary Examiner*—Frank Gonzalez
*Assistant Examiner*—Jason D. Eisenberg
*Attorney, Agent, or Firm*—Ronald R. Snider

[57] ABSTRACT

An optical system for a high-sensitivity reflectivity measurement equipment having a simple structure enhances the light utilization efficiency and simplifies the production process and reduces the cost.

An aspherical concave mirror with a predetermined range opened at the central portion and one focal point set on the outside of the end surface of the opening is used. The region width of the mirror surface measured from the plane the opening is so determined that the incident light from a proper light source and reflected by the mirror surface to enters the sample placed at the focal point at an incident angle $\theta$ where $60° \leq \theta < 90°$. The incident light is reflected by the aspherical concave mirror and the sample surface and again by the aspherical concave mirror so as to become outgoing light for detection. Thus, appropriate and efficient incidence of light to the sample is enabled by a very simple structure having the aspherical concave mirror as the main element. High utilization of effective light is enabled and the detection accuracy is enhanced.

5 Claims, 2 Drawing Sheets

OPTICAL SYSTEM FOR INFRARED SPECTROSCOPY HAVING AN ASPHERICAL CONCAVE MIRROR

FIELD OF THE INVENTION

The present invention relates to an optical system for a high-sensitivity reflectivity measurement equipment and, more especially, to an optical system which is used for a high-sensitivity reflectivity measurement equipment for detecting the incident light which enters a sample at a large incident angle and reflected thereby.

BACKGROUND OF THE INVENTION

Determination of absorbance for estimating a sample on the basis of the absorbance by detecting the light transmitted through the sample is unsuitable for measuring the absorbance of a thin film having a thickness of not more than the wavelength of infrared, for example, by using infrared. As a method effective for infrared spectroscopy, a high-sensitivity reflectivity measurement has recently been known. The high-sensitivity reflectivity measurement is a method of projecting light onto a sample at an incident angle of not less than 60 degrees and less than 90 degrees, and judging the absorbance of light on the surface of the sample by detecting the reflected light.

In a recent infrared spectroscopy, an FT (Fourier-Transform) system is adopted, and the high-sensitivity reflectivity measurement has attracted more and more attention. The adoption of the FT system to infrared spectroscopy has made the infrared spectroscopy applicable to a microscopic measurement, so that various kinds of infrared microscopic measurement equipments are now commercially available. Various methods which are adopted in general infrared spectroscopes have also been applied to a microscopic measurement.

However, it is very difficult to apply the high-sensitivity reflectivity measurement to general infrared microscopic measurements.

A Casegrainian mirror is usually used as the object mirror of a general infrared microscope. In a high-sensitivity reflectivity measurement using the Casegrainian mirror, since it is necessary that the incident angle of light relative to a sample is 60 to 90 degrees, the Casegrainian mirror must have a large angular aperture.

It is possible to produce a Casegrainian mirror having a large angular aperture in principle, but the production is technically very difficult. In addition, since a Casegrainian mirror having a large angular aperture diffuses light in a wide range, the utilization efficiency of light is greatly lowered in comparison with a general Casegrainian mirror. The application of a high-sensitivity reflectivity measurement equipment to a microscopic measurement has not been generalized because an objective mirror type measurement equipment is required in a microscopic measurement, which increases the limitation at the time of installation in comparison with a general measurement equipment. A reflective mirror, especially, a conventional Casegrainian mirror is mostly used as the object mirror of an infrared microscope, but the Casegrainian mirror has a complicated structure and costs high.

The same problems are produced in the case of using a unit equipment adopting the high=sensitivity reflectivity measurement.

SUMMARY OF THE INVENTION

Accordingly, it is a first object of the present invention to eliminate the above-described problems in the related art and to provide an optical system for a high-sensitivity reflectivity measurement equipment which has a simple structure, which can be easily produced and which does not lower the light utilization efficiency, and a microscope using the same.

To achieve this aim, in a first aspect of the present invention, there is provided an optical system for a high-sensitivity reflectivity measurement equipment which has an incident angle $\theta$, where $60° \leq \theta < 90°$; relative to a sample and which detects the light reflected by the sample, the equipment comprising:

an aspherical concave mirror which has an opening at the central portion in a predetermine range, which has one focal point on the outside of the plane of the opening, and the surface region width of which measured from the plane of the opening is so determined that at least part of the light incident from a proper light source and reflected by the mirror surface enters the focal point at the incident angle $\theta$;

wherein the sample is placed at the focal point so that the light receiving surface is! perpendicular relative to the optical axis of the concave mirror, and the outgoing light for detection is the light reflected by the aspherical concave mirror and the light receiving surface of the sample and reflected again by the aspherical concave mirror.

In an optical system for a high-sensitivity reflectivity measurement equipment provided in a second aspect of the present invention, the aspherical concave mirror is an ellipsoidal concave mirror, a first focal point of the two which is the closer to the mirror surface is the focal point at which the sample is placed, the second focal point being the proper light source for the incident light, and the outgoing light for detection is converged on the second focal point.

In an optical system for a high-sensitivity reflectivity measurement equipment provided in a third aspect of the present invention, the aspherical concave mirror is a parabolic concave mirror, and the incident light and the outgoing light to and from the parabolic concave mirror are parallel rays.

In an optical system for a high-sensitivity reflectivity measurement equipment provided in a fourth aspect of the present invention, the aspherical concave mirror is a hyperbolic concave mirror, and the first focal point of the two which is the closer to the mirror surface is the focal point at which the sample is placed, and the incident light to the hyperbolic concave mirror is directed to the second focal point.

In an optical system for a high-sensitivity reflectivity measurement equipment provided in a fifth aspect of the present invention, the aspherical concave mirror is an ellipsoidal concave mirror, a first focal point of the two which is the closer to the mirror surface is the focal point at which the sample is placed, the second focal point being the proper light source for the incident light, the outgoing light for detection is converged on the second focal point, a convex mirror for receiving the light projected from the second focal point is placed between the first and second focal points in such a manner that the central position thereof is situated on the optical axis, a plane mirror having an opening for passing the light projected from the second focal point therethrough and a mirror surface facing the convex mirror is disposed between the convex mirror and the second focal point in such a manner as to be perpendicular relative to the optical axis, and the light projected from the second focal point enters and is reflected from the convex mirror, the plane mirror, the ellipsoidal concave mirror, the sample, the ellipsoidal concave mirror, the plane mirror and the convex mirror in that order and becomes the outgoing light.

In an optical system for a high-sensitivity reflectivity measurement equipment provided in one of the first to fourth aspects of the present invention, an aspherical concave mirror (an ellipsoidal concave mirror, a parabolic concave mirror, or a hyperbolic concave mirror) is used, and the focal points are set on the outside of the end surface of the opening which is formed in a predetermined range of the central portion. This very simple structure enables light to enter a sample at an incident angle of not less than 60 degrees and less than 90 degrees. In other words, by simply setting an aspherical concave mirror, it is possible to reflect the incident light for detection so as to direct the light to the sample surface in an appropriate angular range.

Since the surface width of the aspherical concave mirror is in the range which enables the light projected from an appropriate light source position and reflected by the concave mirror to enter the sample at an incident angle of not less than 60 degrees and less than 90 degrees, it is possible to safely cancel the light which enters at an incident angle out of the above-described range and which does not enable an appropriate high-sensitivity reflectivity measurement.

According to the above-described structure, light enters the part other than the aspherical concave mirror, and also enters the opening portion provided at the central portion of the concave mirror. Such incident light leads to the loss of light. However, in a conventional optical system using a Casegrainian mirror, some rays incident to the central portion of the convex mirror pass through the center opening of the concave mirror and return as they are, and other rays are received and cut by the concave mirror itself. In this way, in the total light incident to the convex light in a conventional optical system using a Casegrainian mirror, especially a Casegrainian mirror having a wide angular aperture, the quantity of light which reaches the sample surface and is reflected as proper outgoing light is much smaller than that in the present invention. Therefore, the utilization efficiency of light is improved in the optical system of the present invention using an aspherical concave mirror in comparison with a conventional one.

According to an optical system for a high-sensitivity reflectivity measurement equipment provided in the fifth aspect of the present invention, a convex mirror with the mirror surface faced toward the second focal point is provided between the ellipsoidal concave mirror and the second focal point, and a plane mirror provided with an opening for passing incident light therethrough is provided between the convex mirror and the second focal point.

The light for detection is projected from the light source provided on the optical axis of the ellipsoidal concave mirror enters and is reflected from the convex mirror, the plane mirror, the ellipsoidal concave mirror and the sample in that order, and enters and is reflected again in the reverse order to become the outgoing light.

According to this structure, although the actual light source is not positioned at the second focal point, it is possible to set the direction of the incident light to the ellipsoidal concave mirror in the same direction of the light outgoing from the second focal point and incident to the ellipsoidal concave mirror by adjusting the positions of the convex mirror and the plane mirror. In this way, the light incident to the ellipsoidal concave mirror enters the sample surface at an appropriate angle (incident angle of not less than 60 degrees and less than 90 degrees) and takes the reverse route to the route for incidence as the outgoing light toward the convergent point.

Since it is possible to set a virtual light source not at the actual light source position but at the second focal point by adjusting the positions of the convex mirror and the plane mirror, the applicability of the optical system to various apparatuses such as a microscope is improved.

The above and other objects, features and advantages of the present invention will become clear from the following description of the preferred embodiments thereof, taken in conjunction with the accompanying drawings.

DESCRIPTION OF THE PREFERRED EMBODIMENTS

The preferred embodiments of the present invention will be explained hereunder with reference to the drawings.

Figure 1:
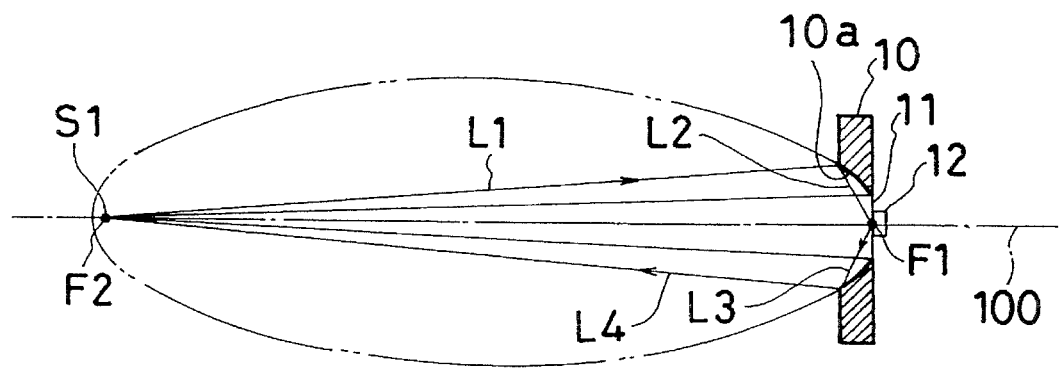
FIG. 1 schematically shows the structure of a first embodiment of an optical system for a high-sensitivity reflectivity measurement equipment according to the present invention in which an ellipsoidal concave mirror is used as an aspherical concave mirror.

FIG. 1 shows a first embodiment of the present invention in which an ellipsoidal concave mirror is used as an aspherical concave mirror.

In FIG. 1, an ellipsoidal concave mirror 10 has first and second focal points F1 and F2, and an opening 11 is formed at the center portion thereof. A sample 12 is disposed at the first focal point F1 in such a manner that the sample surface is perpendicular relative to an optical axis 100.

The present invention is characterized in that the first focal point F1 is positioned on or slightly on the outside of plane of the opening 11 of the ellipsoidal concave mirror 10. That is, a mirror surface 10a of the ellipsoidal concave mirror 10 is precisely formed so as to have the focal point at this position.

A light source S1 is disposed at the second focal point F2. The light L1 projected from the light source S1 is caused to directly enter the mirror surface 10a of the ellipsoidal concave mirror 10. The light L2 reflected by the mirror surface 10a converges on the first focal point F1. In other words, the reflected light L2 enters the surface of the sample 12 which is perpendicular relative to the optical axis 100.

The region width of the mirror surface 10a is so determined that the incident angle of the light from the mirror surface of the ellipsoidal concave mirror 10 to the sample 12 is not less than 60 degrees and less than 90 degrees. The first focal point F1 in this embodiment is set slightly on the outside of the plane of the opening 11, and all the light incident to the mirror surface 10a is caused to enter the surface of the sample 12 in the above-described appropriate angular range. The light L3 reflected by the surface of the sample 12 is reflected again by the mirror surface 10a and converged on the second focal point F2. The structure of the optical system for a high-sensitivity reflectivity measurement equipment at a stage prior to the incident light and the route of the outgoing light at the subsequent stage are the same as those in a conventional optical system for a high-sensitivity reflectivity measurement equipment, and the explanation thereof will be omitted.

In this way, a Simple structure of disposing the ellipsoidal concave mirror 10 enables light to accurately enter the surface of the sample 12 at an angle of not less than 60 degrees and less than 90 degrees, thereby enabling a very efficient high-sensitivity reflectivity measurement. That is, according to this embodiment, since all the light reflected by the mirror surface 10a enters the sample 12 in the appropriate angular rang, it never occurs that the incident light out of the appropriate angle is projected to the sample 12 and, in addition, the detection accuracy is very high. Furthermore, the very simple structure greatly lowers the manufacturing cost, and since only the ellipsoidal concave mirror is used as the reflection surface, complicated optical adjustment is not necessary.

Although the light from the light source S1 is projected on a portion other than the mirror surface 10a, such a loss of light is smaller than in a conventional optical system using a Casegrainian mirror, as described above.

Figure 2:
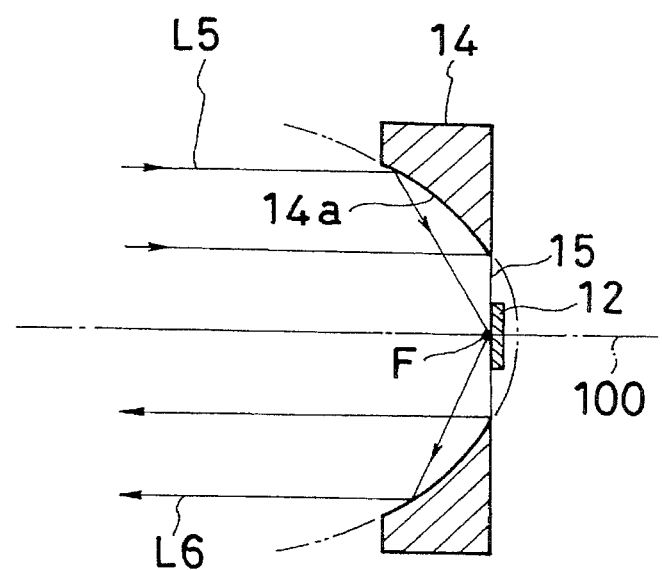
FIG. 2 schematically shows the stature of a second embodiment of an optical system for a high-sensitivity reflectivity measurement equipment according to the present invention in which a parabolic concave mirror is used as an aspherical concave mirror.

FIG. 2 shows a second embodiment of the present invention in which a parabolic concave mirror 14 is used as an aspherical concave mirror. An opening 15 is formed at the center portion of the parabolic concave mirror 14, and the focal point F is set slightly on the outside of the plane of the opening 15. The sample 12 is disposed at the focal point F in the same manner as in the first embodiment shown in FIG. 1.

In the same way as in the first embodiment (surface 10a), the region width of the mirror surface 14a of the parabolic concave mirror 14 is so determined that the parallel light to the optical axis 100 incident to and reflected from the mirror surface 14a of the hyperbolic 14 enters the sample 12 at an angle of not less than 60 degrees and less than 90 degrees. According to this structure, when the parallel light enters the mirror surface 14a, all the incident light is projected to the sample 12 in an appropriate angular range, and the outgoing light L6 reflected by the sample 12 is parallel to the optical axis 100.

Figure 3:
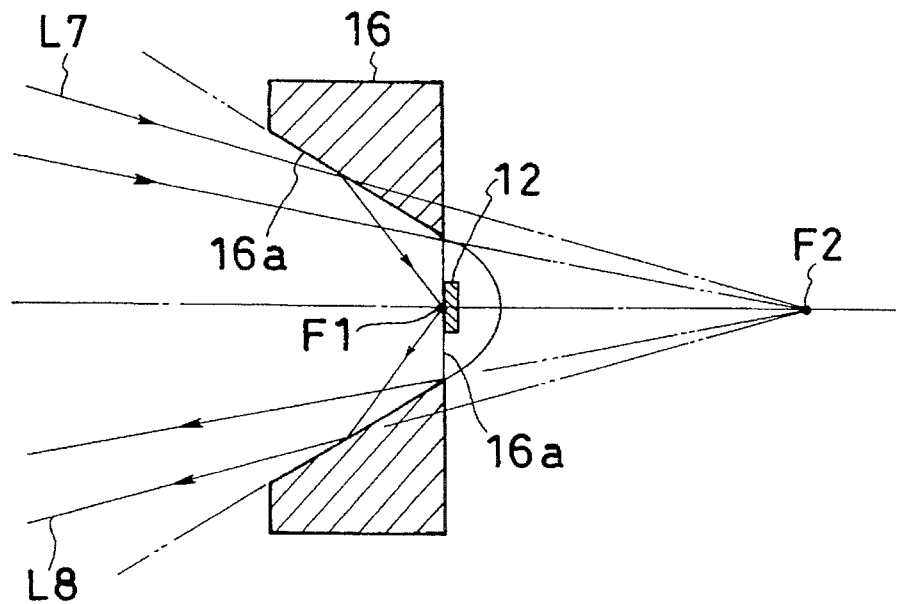
FIG. 3 schematically shows the structure of a third embodiment of an optical system for a high-sensitivity reflectivity measurement equipment according to the present invention in which a hyperbolic is used as an aspherical concave mirror.

FIG. 3 shows a third embodiment of the present invention in which a hyperbolic 16 is used as an aspherical concave mirror.

In the same way as in the first and second embodiments, an opening 16a is formed at the center portion of the hyperbolic 16. The optical system has two focal points in the same way as in the first embodiment. The first focal point F1 closer to the hyperbolic 16 is set slightly on the outside of the plane of the opening 16a, and the sample 12 is disposed at the first focal point. The second focal point F2 is positioned on the further outside of the hyperbolic 16 than the first focal point F1 unlike in the first embodiment.

In this embodiment, incident light L7 enters the mirror surface 16a of the hyperbolic 16 iso as to be converged on the second focal point F2. The region width of the mirror surface 16a is so determined that the incident light L7 reflected by the mirror surface 16a enters the sample 12 at an appropriate angle of not less than 60 degrees and less than 90 degrees. According to this structure, the incident light L7 is reflected by the sample 12 and reflected again by the mirror surface 16a as outgoing light L8. The advantages of the third embodiment are the same as those of the first and second embodiment.

Figure 4:
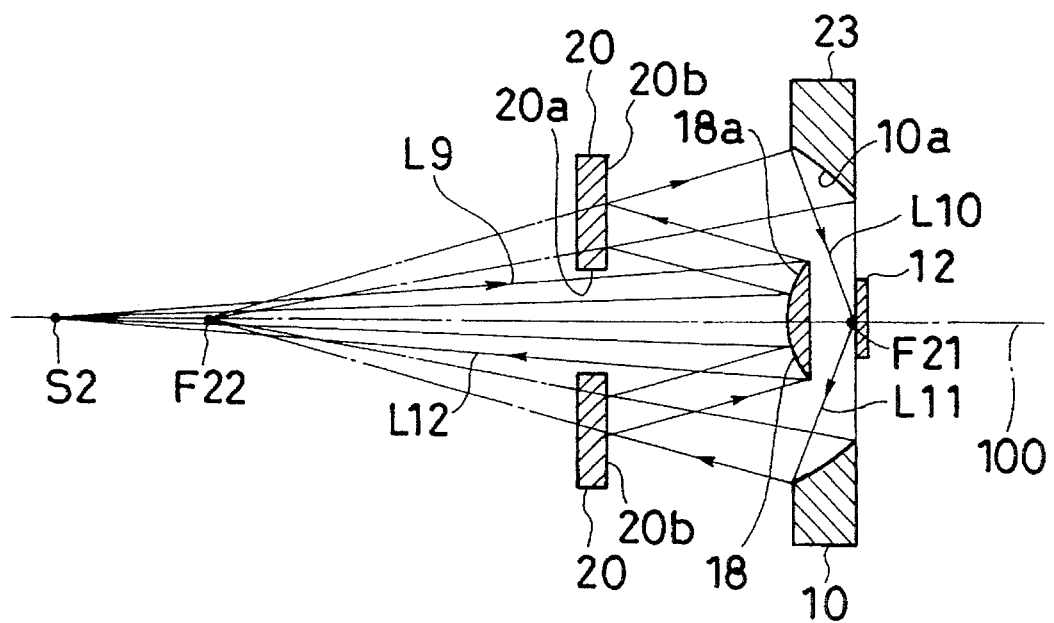
FIG. 4 schematically shows the structure of a fourth embodiment of an optical system for a high-sensitivity reflectivity measurement equipment according to the present invention in which an ellipsoidal concave mirror is used as an aspherical concave mirror.

FIG. 4 shows another embodiment of the present invention in which the ellipsoidal concave mirror 10 is used as an aspherical concave mirror.

In FIG. 4, the ellipsoidal concave mirror 10 has two focal points F21, F22. The first focal point F21 is the same as the first focal point F1 in the first embodiment and the sample 12 is disposed at the first focal point F21 in the same way as in the first embodiment.

A convex mirror ! 8 is disposed between the first focal point F21 and the second focal point F22 in such a manner that the mirror surface 18a faces the second focal point F22 and the central position thereof is situated on the optical axis 100. A plane mirror 20 is disposed between the convex mirror 18 and the second focal point F22 in such a manner that the mirror surface faces the convex mirror 18 and the convex mirror 18 is perpendicular relative to the optical axis 100. An opening 20a for passing incident light therethrough is provided at the central portion of the plane mirror 20.

A light source S2 is disposed on the optical axis 100 at a position outside (on the left side in FIG. 4) of the second focal point F22. Incident light L9) projected from the light source S2 passes through the opening 20a of the plane mirror 20, is reflected by the mirror surface 18a of the convex mirror 18, is further reflected by the mirror surface 20b of the plane mirror 20 and enters the mirror surface 10a of the ellipsoidal concave mirror 10.

The direction of incidence of the light to the mirror surface 10a coincides with the direction in which light is projected from the second focal point F22. This is adjusted by the structure and the position of the convex mirror 18 and the position of the plane mirror 20. This coincidence of the direction of incidence enables all the light L10 reflected by the mirror surface 10a to enter the surface of the sample 12 in an appropriate angular range of not less than 60 degrees to less than 90 degrees. The light L11 reflected by the sample 12 is reflected again by the mirror surface 10a, further by the mirror surface 20b of the plane mirror 20 and the mirror surface 18a of the convex mirror 18, and then converges on the light source S2 as outgoing light L12.

As described above, according to this embodiment, it is possible to cause incident light to enter the sample 12 at an appropriate angle without setting the light source S2 at the second focal point F22. In other words, it is possible to cause light to enter from a virtual light source set at the second focal point so as to project the light to the sample 12 at an appropriate position.

In this way, since there is a certain degree of freedom in the position of the light source, the applicability of the optical system to various apparatuses is improved.

In addition, according to this embodiment, since it is possible to design the entire structure such that most part of the light reflected by the convex mirror 18 enters in an appropriate angular range, it is easy to improve the light utilization efficiency.

In each of the above-described embodiments, since all the light incident from an appropriate light source to a mirror surface converges on the focal point at which the sample is disposed, it is possible to obtain the accurate result of detection with high efficiency. Although it is required to precisely adjust the focal point of such a concave mirror, it is possible to produce such a concave mirror with easiness by using a recent precision lathe having a very high precision.

The case of setting an optical system of the present invention as an objective of an infrared microscope for high-sensitivity reflectivity measurement will now be explained.

In the case of applying an optical system of the present invention, the problems are that the sample must be set at the focal point of a concave mirror, and that since the incident angle to the sample is large in such high-sensitivity reflectivity measurement, it is impossible to visually observe the sample with a high magnification. It is therefore preferable to use a resolver which enables a multiplicity of objectives to be attached and to be switched in the same way as in a general visible microscope. That is, it is preferable to set in a resolver an ordinary visual lens or a Casegrainian mirror for general measurement so as to be switchable with an optical system of the present invention.

Thus, by switching the microscope after general observation to a high-sensitivity reflectivity measurement equipment using an optical system of the present invention, high-sensitivity reflectivity measurement with high utilization efficiency by the optical system of the present invention having a simple structure is possible as well as visual observation by using the microscope.

As explained above, according to an optical system for a high-sensitivity reflectivity measurement, it is possible to produce an optical system for a high-sensitivity reflectivity measurement having a high light utilization efficiency by a very simple structure mainly composed of a single aspherical concave mirror. Since all the light projected from an appropriate position to the mirror surface of a concave mirror is incident to the sample in an appropriate incident angular range, the accuracy of the result of detection by reflected light is enhanced.

While there has been described what are at present considered to be preferred embodiments of the invention, it will be understood that various modifications may be made thereto, and it is intended that the appended claims cover all such modifications as fall within the true spirit and scope of the invention.

What is claimed is:

1. An optical system for a high-sensitivity reflectivity measurement equipment which detects reflected light, the equipment comprising:

an aspherical concave mirror having an optical axis and which has an opening at its central portion in a predetermined range, which has one focal point outside of a plane of said opening, and having a mirror surface region width which is measured from said plane of said opening and which is determined so that at least a part of light incident from a proper light source and reflected by said mirror surface passes through said focal point at an incident angle θ, where $60° \leq θ < 90°$;

wherein said sample is placed at said focal point so that a light receiving surface is perpendicular relative to the optical axis of said concave mirror, and outgoing light for detection is light reflected by said aspherical concave mirror and said light receiving surface of said sample and reflected against said aspherical concave mirror.

2. An optical system for a high-sensitivity reflectivity measurement equipment according to claim 1, wherein:

said aspherical concave mirror is an ellipsoidal concave mirror;

a first focal point at which said sample is placed which is closer to a mirror surface of said ellipsoidal concave mirror than a second focal point where a light source for incident light is located; and outgoing light for detection is converged on said second focal point.

3. An optical system for a high-sensitivity reflectivity measurement equipment according to claim 2, further comprising:

a convex mirror for receiving light projected from said second focal point which is placed between said first and second focal points with a central position thereof situated on said optical axis; and a plane mirror having an opening for passing the light projected from said second focal point therethrough and a mirror surface facing said convex mirror is disposed between said convex mirror and said second focal point and is disposed perpendicular relative to said optical axis; wherein light projected from aid second focal point enters and is reflected from said convex mirror, said plane mirror, said ellipsoidal concave mirror, said sample, said ellipsoidal concave mirror, said plane mirror and said convex mirror in that order and becomes outgoing light.

4. An optical system for a high-sensitivity reflectivity measurement equipment according to claim 1, wherein:

said aspherical concave mirror is a parabolic concave mirror; and incident light to and outgoing light from said parabolic concave mirror are parallel rays.

5. An optical system for a high-sensitivity reflectivity measurement equipment according to claim 1, wherein:

said aspherical concave mirror is a hyperbolic concave mirror having a surface;

a first focal point which is closer to the mirror surface of said hyperbolic concave mirror and wherein said sample is placed at said first focal point; and incident light to said hyperbolic concave mirror is directed to a second focal point.

* * * * *